(12) United States Patent
Commarieu et al.

(10) Patent No.: US 9,260,957 B2
(45) Date of Patent: Feb. 16, 2016

(54) USE OF NANOPARTICLES FOR LABELLING OIL FIELD INJECTION WATERS

(75) Inventors: Annie Commarieu, Lacq/Atrix (FR);
Fabrice Aubertin, Pau (FR); Nicolas Crowther, Saint-quentin-fallavier (FR);
Cédric Louis, Saint-quentin-fallavier (FR); Pascal Perriat, Villeubbanne (FR);
Matteo Martini, Villeurbanne (FR);
Olivier Tillement, Villeurbanne (FR)

(73) Assignee: Total SA, Courbevoie (FR)

( * ) Notice: Subject to any disclaimer, the term of this patent is extended or adjusted under 35 U.S.C. 154(b) by 559 days.

(21) Appl. No.: 13/518,827

(22) PCT Filed: Dec. 22, 2010

(86) PCT No.: PCT/EP2010/070552
§ 371 (c)(1),
(2), (4) Date: Dec. 18, 2012

(87) PCT Pub. No.: WO2011/076874
PCT Pub. Date: Jun. 30, 2011

(65) Prior Publication Data
US 2013/0084643 A1    Apr. 4, 2013

(30) Foreign Application Priority Data

Dec. 24, 2009 (FR) .................. 09 59608

(51) Int. Cl.
*G01N 21/64* (2006.01)
*E21B 47/00* (2012.01)
(Continued)

(52) U.S. Cl.
CPC . *E21B 47/00* (2013.01); *C09K 8/03* (2013.01);
*C09K 8/58* (2013.01); *C09K 11/592* (2013.01);
(Continued)

(58) Field of Classification Search
CPC ....... E21B 47/00; C09K 11/592; G01N 21/64
USPC ................................... 436/25, 27–28
See application file for complete search history.

(56) References Cited

U.S. PATENT DOCUMENTS 6,645,769 B2 * 11/2003 Tayebi et al. .................. 436/56
2004/0101822 A1 * 5/2004 Wiesner et al. ................. 435/5
(Continued)

OTHER PUBLICATIONS

Xu, H. et al., Journal of Biomedical Materials Research 2003, 66A, 870-879.*
(Continued)

*Primary Examiner* — Arlen Soderquist
(74) *Attorney, Agent, or Firm* — Patterson Thuente Pedersen, P.A.

(57) ABSTRACT

The present invention relates to the development of tracer fluids, more generally, that of aqueous liquids, intended to be injected under pressure in an oil reservoir, for example from an injection well up to a production well.
The object of the invention is to propose a new method of study of a solid medium, i.e. an oil reservoir, by diffusion of a liquid (i.e. injection waters) containing tracers, through said solid medium, which is simple to implement and economical and which remedies the drawbacks of the known tracers for injection waters of oil reservoirs.
This method essentially consisting of injecting, in this solid medium, an injection liquid comprising a nanoparticle-based tracer having average dimensions comprised between 20 and 200 nm, detectable by means of one or several S signals at dilutions of less than or equal to $10^{-7}$, adapted to form a stable colloidal suspension in a saline medium, at least a portion of which is constituted of a core and a coating provided with an adjustable hydrophilic-lipophilic balance (HLB) and comprising at least one organic and/or organosilicon component; recovering the liquid having diffused; and analyzing this liquid having diffused to measure the quantity of tracer by detection of the signal or signals S.

17 Claims, 3 Drawing Sheets

(51) Int. Cl.
*C09K 8/03* (2006.01)
*C09K 8/58* (2006.01)
*E21B 47/10* (2012.01)
*C09K 11/59* (2006.01)
*B82Y 15/00* (2011.01)

(52) U.S. Cl.
CPC ............ *E21B 47/1015* (2013.01); *G01N 21/64* (2013.01); *B82Y 15/00* (2013.01); *Y10S 977/773* (2013.01); *Y10S 977/902* (2013.01)

(56) References Cited

U.S. PATENT DOCUMENTS

| | | | | |
|---|---|---|---|---|
| 2006/0029802 | A1* | 2/2006 | Ying et al. | 428/403 |
| 2006/0228554 | A1* | 10/2006 | Tan et al. | 428/404 |
| 2008/0076119 | A9* | 3/2008 | Sun et al. | 435/6 |
| 2008/0258115 | A1* | 10/2008 | Ying et al. | 252/500 |
| 2009/0069481 | A1* | 3/2009 | Zhang et al. | 524/413 |
| 2009/0087911 | A1* | 4/2009 | Ramos | 436/27 |
| 2009/0087912 | A1* | 4/2009 | Ramos et al. | 436/27 |
| 2010/0255311 | A1* | 10/2010 | Lee et al. | 428/403 |
| 2011/0027375 | A1* | 2/2011 | Tillement et al. | 424/497 |
| 2011/0073811 | A1* | 3/2011 | Ying et al. | 252/500 |
| 2012/0142111 | A1* | 6/2012 | Tour et al. | 436/27 |

OTHER PUBLICATIONS

Ye, Z. et al., Analytical Chemistry 2004, 76, 513-518.*
Kobayashi, Y. et al., Journal of Colloid and Interface Science 2005, 283, 392-396.*
Ju, B. et al., China Particuology 2006, 4, 41-46.*
Bagwe, R. P. et al., Langmuir 2006, 22, 4357-4362.*
De Palma, R. et al., Chemistry of Materials 2007, 19, 1821-1831.*
Rampazzo, E. et al., Journal of the American Chemical Society 2007, 129, 14251-14256.*
Liu, Z. et al., Chemical Comminications 2008, 694-696.*
Han, Y. et al., Langmuir 2008, 24, 5842-5848.*
Kanj, M. et al., Clean Technology 2008, 506-509.*
Heitsch, A. T. et al., Journal of Solid State Chemistry 2008, 181, 1590-1599.*
Wu, W. et al., Nanoscale Research Letters 2008, 3, 397-415.*
Koole, R. et al., Bioconjugate Chemistry 2008, 19, 2471-2479.*
Wang, F. et al., Chemical Society Reviews 2009, 38, 976-989.*
Kanj, M. Y. et al., SPE-126161 2009, 11 pages.*
Fernandez-Lopez, C. et al., Langmuir 2009, 25, 13894-13899.*
He, F. et al., Journal of Colloid and Interface Science 2009, 334, 96-102.*
Saleh, N. et al., Environmental Science and Technology 2009, 42, 3349-3355.*
Rodriguez, E. et al., SPE-124418-MS 2009, 21 pages.*

* cited by examiner

USE OF NANOPARTICLES FOR LABELLING OIL FIELD INJECTION WATERS

The field of this invention is that of the exploration and the exploitation of oil reservoirs.

More precisely, this invention relates to the development of tracer fluids, more generally, that of aqueous liquids, intended to be injected under pressure in an oil reservoir, for example from an injection well up to a production well.

The injected waters thus diffuse through the geological solid medium, which constitutes the oil reservoir, making it possible to study the latter by following the path of the injected waters. The goal is in particular to control the flows between the injection well(s) and the production well(s) and/or to evaluate the volumes of oil in reserve in the reservoir and, in fine, of optimizing the oil exploration and exploitation.

TECHNOLOGICAL BACKGROUND

It is well-known in the exploitation of an oil reservoir that, most of the time, no more than half of the oil initially present in the reservoir is extracted, or even less. The recovery by the primary means, that is, the use of extraction energy utilized from gases or liquids present in the subsoil and currently, initially, a certain pressure in the reservoir, allows for only extracting low percentages of the total oil present in the reservoir. To complete this primary recovery, one proceeds with a secondary recovery consisting in implementing what is called a "water drive" or "water flooding" production, that is, by injecting water in a well (injection well) at a location of the reservoir, so as to push the oil of the reservoir out of the subsoil, by at least one other called a "production well".

To improve the secondary recovery by water drive, it is known to add surfactants to the injection water. This technique for optimizing the oil recovery by pushing injected water, to which surfactants may or may not have been added, also involves tracers that can be easily detected in the liquid, namely the injection water and push water at the exit of production wells. These tracers allow for measuring the arrival time, that is, the time which passes between the injection of the injection and push waters in the injection well(s) and the moment when these injection water and push water charged in tracers come out at the exit of one of several isolated production wells. From this arrival time, one can determine the volume of the reservoir that constitutes the oil reservoir. This is one of the most important parameters which can be determined by the use of tracer fluids, since it allows, on the one hand, adjusting the quantity of surfactant introduced in the injection and push waters, and on the other hand, evaluating the additional quantity of oil that can be expected following the implementation of this optimized method for recovering oil. As long as the fluid containing the tracer has been detected at the production well(s), the method of study for analyzing, monitoring, and optimally recovering oil requires the concentration of tracers in the fluid produced at the exit to be measured, continuously or not, so as to be able to plot the curves of tracer concentration as a function of the time or as a function of the volume of fluid produced.

Tracers in the injection water and push waters for oil reservoirs also enable detecting aberrations in the flow rates caused by pressure differentials in the reservoir, which are caused by factors other than the injection of injection and push waters and which hinder the performances.

The specifications of the tracers, usable in these injection and push waters for optimizing oil recovery comprise the following characteristics:

economical;

compatible with the fluids which are naturally present in the reservoir and with the oil-reservoir rock itself as well as with the fluids injected in the reservoir, namely, the injection and push liquids (waters);

easy qualitative and quantitative detection of the tracer no matter the materials present in the fluid at the exit of the production well. For example, an aqueous solution of sodium chloride cannot be used as tracer since most of the oilfields contain sea water, and thus a substantial quantity of sodium chloride, which makes detecting NaCl chloride used as tracer particularly difficult;

furtive tracer, that is, not easily absorbed in the solid medium traversed or eliminated from the tracing fluid, since with the analytical technique used, the tracer concentration in the fluids produced at the exit is determined and compared with that of the fluids injected in the injection well(s);

the tracer resists bacterial contamination, high temperatures and high pressures present in oil reservoirs;

the tracer has the ability to interact or not interact with the medium of the reservoir, namely, the geological media, oil-bearing or not;

access to a great number of tracers and different codings for possible simultaneous detections (several injection wells) or tracing test which are successive over time.

Regarding the state of the art relating to such tracers for injection and push waters (tracing fluid) making it possible to probe oil reservoirs by diffusion between an injection well and a production well, one can cite the U.S. Pat. Nos. 4,231,426-B1 and 4,299,709-B1, which disclose aqueous tracer fluids comprising from 0.01 to 10% in weight of a nitrate salt associated with a bactericidal agent chosen among aromatic compounds (benzene, toluene, xylene).

The Canadian patent application CA 2 674 127-A1 relates to a method consisting in using a natural isotope of carbon 13 for identifying premature drilling of injection waters in oil wells.

In addition, there are a dozen families of molecules adapted and currently identified as tracers for injection waters in oil reservoirs. These molecule families are, for example, fluorinated benzoic acids or naphtalenesulfonic acids.

The tracer molecules which are known and used have a specific chemical/radioactive signature. These known tracers can be detected with great sensitivity. However, they have three major drawbacks:

their quantification requires a rather complex and expensive process and can be carried out only in a specialized center, often far away from productions sites;

these molecules, which are not numerous, do not allow for multi-labeling or repeated labelings;

some of these known tracers are caused to disappear due to their negative impact on the medium.

Furthermore, the site "*Institute for Energy Technology*" (IFE) has put online to date a PowerPoint presentation entitled SIP 2007-2009 "*New functional tracers based on nanotechnology and radiotracer generators Department for Reservoir and Exploration Technology*". In particular, this document discloses the use of surface-modified nanoparticles as tracers for flow monitoring in oil reservoirs, oil wells and in process systems. More precisely yet, this presentation describes functionalized tracer nanoparticles comprising a $Gd_2O_3$-based core and a siloxane-based surface coating which is functionalized with additional molecules. The rare earth core and/or the additional molecules can emit light signals by fluorescence or radioactive signals.

However, to date, no study has shown the feasibility of the detection of particles for oil tracing. It seems to be even generally accepted that particles, due to the volume of space they fill, are filtered and strongly retained in the soil, thus preventing any reasonable use of their detection as tracing. It is actually based on this hypothesis that the above-mentioned PowerPoint presentation from IFE is based. In fact, this document does not make any reference to the detection of particles, but rather to the detection of a by-product or a residue related to the degradation of these particles.

In a completely different field, the French patent application FR 2 867 180-A1 describes hybrid nanoparticles comprising, on the one hand, a core made of rare earth oxides, optionally doped with rare earth or actinide or a mixture of rare earths or a mixture of rare earths and actinide, and, on the other hand, a coating around this core, said coating chiefly consisting of polysiloxane functionalized by at least one biological ligand grafted by covalent bonding. The core can be made of $Gd_2O_3$ doped with an amount of $Tb^{3+}$ or by uranium and the polysiloxane coating can be achieved by making an aminopropyltriethoxysilane, a tetraethylsilicate, and a triethylamine react. These nanoparticles are used as probes for the detection, the monitoring, and the quantification of biological systems.

The French patent application FR 2 922 106-A1 relates to the same technical field and targets the use of these nanoparticles as radiosensitizing agents for making the radiotherapy more efficient. The size of these nanoparticles is comprised between 10 and 50 nanometers.

TECHNICAL PROBLEM AND OBJECTIVES TO ACHIEVE

In this context, the present invention aims at meeting at least one of the following objectives:
- propose a new method of study of a solid medium, for example an oil reservoir, by diffusion of a liquid through said solid medium, which is simple to implement and economical;
- remedy the drawbacks of the tracers for injection waters of oil reservoirs according to the prior art;
- provide a tracer which follows perfectly the injection waters in their diffusion (percolation) through solid media that constitute the oil reservoirs, without presenting any interaction with the geological subsoil which is traversed (neither attraction nor repulsion);
- provide a tracer for injection water of oil reservoirs whose interactions (attraction-repulsion) vis-à-vis the geological medium through which it percolates, are intentionally controllable;
- provide a new furtive tracer for injection waters of oil reservoirs;
- provide a new tracer for injection waters of oil reservoirs having a sensitivity and/or easy of detection that is substantially enhanced with respect to the tracers known up to this day;
- provide a new tracer for injection waters of oil reservoirs having several easily detectable signals to carry out a multi-detection and multiply the analyses in a time period or space;
- provide a new tracer for injection waters of oil reservoirs and co-compatible;
- provide a new tracer for injection waters of oil reservoirs stable in a physical, chemical, and biological plane in the geological solid media which constitute the oil reservoirs;
- provide a new liquid, in particular new injection waters, for oil reservoirs that are usable particularly in a method of study of a solid medium, for example an oil reservoir, by diffusion of said liquid through said solid medium;
- provide a new method allowing for optimizing flow control between at least one injection well and at least one production well in an oil reservoir and/or evaluate the volumes of oil in reserve in the reservoir.

BRIEF DESCRIPTION OF THE INVENTION

These objectives, among others, are achieved by the invention which firstly relates to a method of study of a solid medium, for example an oil reservoir, by diffusion of a liquid through said solid medium, characterized in that it essentially consists in:
- injecting, in this solid medium (diffusion), a liquid (injection liquid) comprising a nanoparticle-based tracer;
  - having average sizes comprised, in preferred ascending order, between 20 and 200 nm, 20 and 100 nm, 50 and 100 nm, 60 and 80 nm;
  - detectable by means of one or several S signals at dilutions of less than or equal to $10^{-7}$, preferably $10^{-9}$;
  - adapted to form a stable colloidal suspension in a saline medium;
  - a portion at least of which is constituted of a core and a coating provided with an adjustable hydrophilic-lipophilic balance (HLB) and comprising at least one organic and/or organosilicon component.
- recovering the liquid having been diffused;
- analyzing this liquid having been diffused to measure the quantity of tracer by detection of the signal or signals S.

The invention secondly relates to an injection liquid in an oil reservoir usable particularly in the above-mentioned method characterized in that it comprises a nanoparticle-based tracer:
- having dimensions comprised, preferably in ascending order, between 20 and 200 nm, 20 and 100 nm, 50 and 100 nm, 60 and 80 nm;
- detectable by means of one or several S signals at dilutions of less than or equal to $10^{-7}$, preferably $10^{-9}$;
- adapted to form a stable colloidal suspension in a saline medium;
- a portion at least of which is constituted of a core and a coating provided with an adjustable hydrophilic-lipophilic balance (HLB) and/or an adjustable Zeta potential, and comprising at least one organic and/or organosilicon component.
- the hydrophilic-lipophilic balance (HLB) and/or a Zeta potential of said liquid which can also be adjustable.

The invention thirdly relates to the use of nanoparticles such as defined hereinabove, as tracers in injection water of an oil reservoir, which are intended for the study of said reservoir by diffusion through the latter, in view particularly of monitoring the flows between an injection well and a production well and/or of evaluating the volumes of oil in reserve in the reservoir.

This new technology according to the invention:
- offers a great sensitivity of detection, in particular optical;
- allows also for rapidly and simply analyzing, directly in the oil exploration and exploitation sites, tracers present at concentrations of less than the ppm and even on the order of the ppb;
- is advantageous, particularly due to the simplicity of concentration of the tracer agents which are the nanoparticles, by tangential filtration or dialysis for example;

makes it also possible to purify and separate, in a simple manner, the tracers from the oil residues;

offers a good sensitivity to detection as well as the possibility of extracting in a simple manner the fluorescence signal of the tracers of fluorescence noise of the organic compounds connected, in particular, to oil residues, by time-resolved analysis;

and also offers a system of tracers comprising at least two detection signals, that is, at least two codes adapted to two supplementary detection techniques: nanoparticles constituted of a core made of noble metal or rare earth elements (detectable by ICP chemical analysis, for example) and of a silicon coating comprising at least one detection signal, for example a fluorescent signal.

DETAILED DESCRIPTION OF THE INVENTION

Method of Study of a Solid Medium

The solid medium is preferably an oil reservoir contained in a subsoil (e.g. rocks) which can be of varied geological nature.

The Nanoparticles:

The size analysis of the nanoparticles of the tracer is, for example, measured by means of a commercial granulometer, namely: a Malvern granulometer, the Zetasizer Nano-S, based on PCS (Photon Correlation Spectroscopy).

These nanoparticles are detectable, which means that their presence, or lack thereof, can be identified in the medium beyond a certain concentration and that their concentration can even be quantified as long as they are present in the medium.

These nanoparticles are adapted to form a stable colloidal suspension in a saline medium, which does not settle much. For example, this suspension does not present any precipitation or agglomeration as time goes by, i.e., after 6 months at room temperature.

According to an advantageous embodiment of this method, the core of the nanoparticles contains:

at least one material selected from the group consisting of: the semiconductors, noble metals (e.g. Au, Ag, Pt), fluorides, vanadates, or rare earth oxides and their mixtures and/or alloys; preferably among the lanthanides, their alloys and their mixtures, and, even more preferably, from the sub-groups consisting of: Pr, Nd, Sm, Eu, Tb, Dy, Ho, Er, Tm, and Yb, and their mixtures and/or alloys.

or a matrix, preferably transparent, selected from the group of materials consisting of: silicas, polysiloxanes, aluminas, zirconias, aluminates, aluminophosphates, metal oxides (for example $TiO_2$, $ZnO$, $CeO_2$, $Fe_2O_3$, ...) and their mixtures and/or alloys.

this matrix including within itself and/or at its surface:

i. luminescent entities selected from the group consisting of: the semiconductors, oxides, rare earth fluorides or vanadates, organic fluorescent molecules (preferably fluorescein and/or rhodamine), transition metal ions, rare earth ions connected, or not, to complexing molecules and/or to molecules allowing for enhancing their absorption and their mixtures and/or alloys.

ii. optionally other entities allowing for modifying the luminescence properties and selected from the group consisting of: noble metal particles and their mixtures and/or alloys;

iii. and the mixtures of these entities (i) and (ii).

Regarding the coating of the nanoparticles, it is preferable for it to comprise grafted R-radicals, preferably by covalence, preferably based on surface silanes Si—R connections and originating from:

i. optionally charged hydrophilic compounds, preferably organic hydrophilic compounds having a molecular mass of less than 5,000 g/mol and, even better, less than 450 g/mol, preferably selected from the organic compounds consisting of at least one of the following functions: alcohol, carboxylic acid, amine, amide, ester, ether oxide, sulfonate, phosphonate and phosphinate, and the mixtures of these optionally charged hydrophilic compounds, ii. neutral hydrophilic compounds, preferably a polyalkylene glycol, even more preferably, a polyethylene glycol, a Diethylene-TriaminePentaAcetic acid (DTPA), dithiolate DTPA (DTDTPA) or succinic acid, and the mixtures of these neutral hydrophilic compounds, iii. of one of several compounds, preferably of polymers, hydrophobic;

iv. or of their mixtures.

Advantageously, this nanoparticle coating comprises grafted R-radicals at the rate of at least one R-radical for 10 $nm^2$ of surface, preferably at least one for 1 $nm^2$.

Interactions

To monitor the interactions between, on the one hand, the solid medium to be studied, namely, for example, the geological sub-soil (i.e. rocks) containing the oil reservoir and, on the other hand, the nanoparticles, it is possible, according to an advantageous provision of the invention, to adjust the HLB and/or the Zeta potential of the nanoparticle coating comprising the tracer based on said nanoparticles as a function of the solid medium to be studied.

To do so, for example, either a same surface charge for the nanoparticles and the rocks of the solid medium is provided in order to create a repulsion and limit interactions, or the respective charges are modulated so the nanoparticles and the rocks of the solid medium interact in a controlled and/or specific manner with respect to certain rocks.

Methodology

According to a remarkable embodiment of the method according to the invention, prior to the analysis of the liquid having diffused, the latter is concentrated, preferably by filtration or dialysis, and, even more preferably, by tangential filtration and preferably by the use of a membrane using cutoffs of less than 100 kDa.

To measure the quantity of tracer in the liquid having diffused, detection by fluorescence and/or by chemical analysis and/or by ICP and/or by magnetic analysis (magnetic transition temperature, for example of Curie or Néel) is favored.

According to a variation for measuring the quantity of tracer in the liquid having diffused, one proceeds with at least one detection by time-resolved fluorescence, that is, triggered with delay after excitation (i.e. a few microseconds), which eliminates a large portion of the luminescence, intrinsic to the studied solid medium and measures only that relative to the tracing nanoparticle.

Signals S to be Detected

Preferably, each of at least one portion of the tracing nanoparticles comprises at least two (preferably two) signals to be detected:

a signal S1 that can be emitted by fluorescent compounds and/or by chemiluminescent compounds and measured by fluorescence and/or by chemilimunescence;

a signal S2 that can be emitted by a noble metal (such as gold, silver, platinum, and their mixtures and/or alloys), and measured by chemical analysis and/or ICP and/or magnetic analysis and/or susceptibility measurement, and/or measures of transition temperatures, and/or by analysis of FC/ZFC curves;

said noble metal preferably constituting the core of the nanoparticle.

Injection Liquid (Waters) for the Study of a Solid Medium, i.e. an Oil Reservoir According to another one of these objects, the invention relates to a new injection liquid in an oil reservoir usable, in particular, in the method defined hereinabove, characterized in that it comprises a nanoparticle-based tracer:

having average sizes comprised, in preferred ascending order, between 20 and 200 nm, 20 and 100 nm, 50 and 100 nm, 60 and 80 nm;

detectable by means of one or several S signals at dilutions of less than or equal to $10^{-7}$, preferably $10^{-9}$;

adapted to form a stable colloidal suspension in a saline medium;

at least a portion of which is constituted of a core and a coating provided with an adjustable hydrophilic-lipophilic balance (HLB) and/or an adjustable Zeta potential and comprising at least one organic and/or organosilicon component.

the hydrophilic-lipophilic balance (HLB) and/or a Zeta potential of said liquid which can also be adjustable.

Advantageously, this liquid comprises water and the nanoparticles which it contains are such as defined hereinabove.

Use of the Nanoparticles

According to another one of these objects, the invention relates to a new use of the nanoparticles such as defined hereinabove as tracers in injection waters of an oil reservoir intended for the study of said reservoir by diffusion of these injection waters through said reservoir, particularly for monitoring the flows between an injection well and a production well and/or evaluating the volumes of oil in reserve in the reservoir.

EXAMPLES

PREPARATION 1. SILICA PARTICLES (DIAMETER 64 NM) ENCAPSULATING FLUORSCEIN MOLECULES

In a 2.5 ml bottle, 20 mg of FITC (fluorescein-isothiocyanate) and of APTES ((3-AminoPropyl)TriEthoxySilane) are inserted and vigorously agitated. After 30 minutes of homogenization at room temperature, the synthesis by microemulsion can begin.

In a 100 ml Erlenmeyer flask, 2.27 ml of Triton X-100 (surfactant), 2.31 ml of n-hexanol (co-surfactant), 9.61 ml of cyclohexane and 0.61 ml of water with a pH of 5.5 are inserted and vigorously agitated. After 5 minutes, 0.040 ml of solution containing the fluorescein is added to the microemulsion, then 0.020 ml of APTES and 0.289 ml of TEOS (TetraEthOxyXilane).

Figure 1:
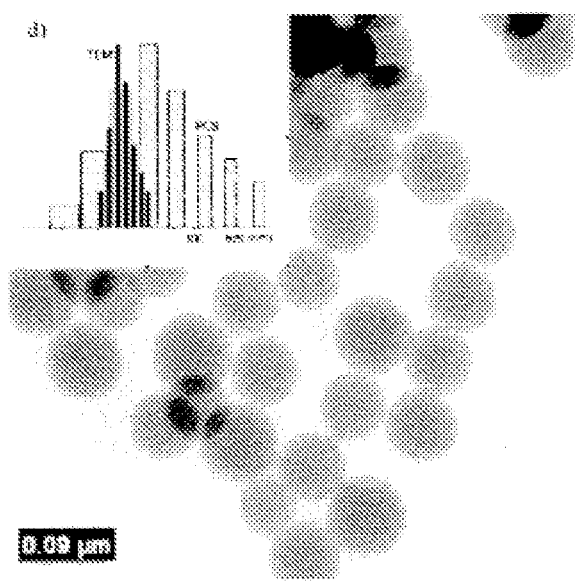
FIG. 1 shows the silica particles (diameter 64 nm) of preparation 1 encapsulating fluorescein molecules (observation with a transmission electron microscope of the JEOL 2010 type operating at 200 kV). This drawing 1 also comprises a particle-size range measured by PCS with a Malvern granulometer Zetasizer Nano-S, on the abscissa, the size of the particles in μm. In this range, TEM means "Transmission Electron Microscopy" and PCS means "Photon Correlation Spectroscopy".

The silica polymerization reaction is completed by the addition of 0.173 ml of $NH_4OH$ (aqueous solution at 25%) after 30 minutes. The microemulsion system continues during 24 hours under agitation at room temperature. After 24 hours, the particles formed (FIG. 1) are recovered by precipitation in centrifugation tubes by adding the same volume of ethanol for each wash. The washes are repeated three times with absolute ethanol. The obtained powder is finally dispersed in 20 ml of distilled water.

PREPARATION 2. SILICA PARTICLES (DIAMETER 58 NM) OF THE CORE-SHELL TYPE WITH A GOLD CORE (DIAMETER 6 NM) AND A SILICA SHELL ENCAPSULATING FLUORSCEIN MOLECULES

In a 2.5 ml bottle, 20 mg of fluorescein (FITC) and of APTES are inserted and vigorously agitated. After 30 minutes of homogenization at room temperature, the synthesis by microemulsion can begin.

In a 100 ml Erlenmeyer flask, 2.10 ml of Triton X-100 (surfactant), 2.14 ml of n-hexanol (co-surfactant), 8.91 ml of cyclohexane (oil), and 1.4 ml of aqueous solution containing 0.595 ml of 16.7 mM $HAuCl_4.3H_2O$, 0.595 ml of 32.8 mM MES (sodium-2-mercaptoethanesulfonate) and 0.198 ml of 412 mM NaBH4, are inserted and vigorously agitated. After 5 minutes, 0.040 ml of solution containing the fluorescein is added to the microemulsion, then 0.020 ml of APTES and 0.289 ml of TEOS (TetraEthOxyXilane).

Figure 2:
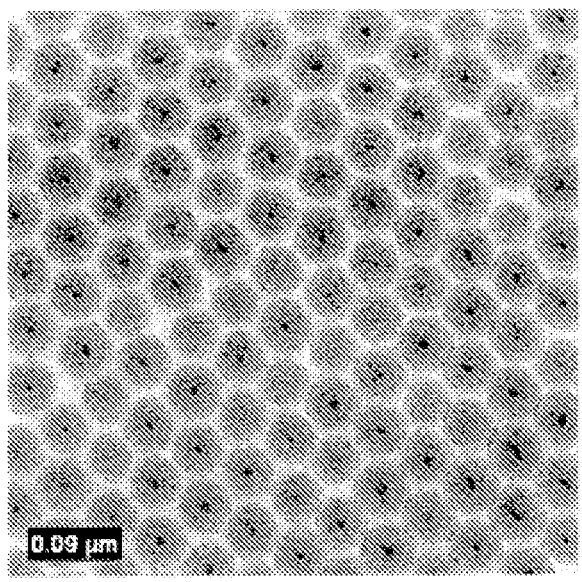
FIG. 2 shows the silica particles (diameter 58 nm) of preparation 2 of the core-shell type with a gold core (diameter 6 nm) and a silica shell encapsulating fluorescein molecules (observation with a transmission electron microscope of the JEOL 2010 type operating at 200 kV).

The silica polymerization reaction is completed by the addition of 0.173 ml of NH4OH after 30 minutes. The microemulsion system continues during 24 hours while agitated at room temperature. After 24 hours, the particles formed (FIG. 2) are recovered by precipitation in centrifugation tubes by adding the same volume of ethanol for each wash. The washes are repeated three times with some absolute ethanol. The obtained powder is finally dispersed in 20 ml of distilled water.

PREPARATION 3. SILICA PARTICLES (DIAMETER 64 NM) ENCAPSULATE POLYDENTATE CHELATES OF $EU^{3+}$

In a 10 ml bottle, 400 mg of DTPA (DiethyleneTriaminePentaAcetic acid), 360 mg of $EuCl_3.7H_2O$ and 5 ml of water whose pH is adjusted to be 8, are inserted.

In a 100 ml Erlenmeyer flask, 2.27 ml of Triton X-100 (surfactant), 2.31 ml of n-hexanol (co-surfactant), 9.61 ml of cyclohexane, and 0.60 ml of the solution containing the DTPA and $Eu^{3+}$ are inserted and vigorously agitated. After 5 minutes, 0.200 ml of TEOS is added to the microemulsion.

The silica polymerization reaction is completed by the addition of 0.050 ml of a solution of $NH_4OH$ after 30 minutes. The microemulsion system is maintained during 24 hours under agitation at room temperature. After 24 hours, the particles formed are recovered by precipitation in centrifugation tubes by adding the same volume of ethanol for each wash. The washes are repeated 3 times with absolute ethanol. The obtained powder is finally dispersed in 20 ml of distilled water.

PREPARATION 4. SILICA PARTICLES (DIAMETER 64 NM) ENCAPSULATING CHELATES OF THE TERBIUM PYRIDINE TYPE

In a 10 ml bottle, 500 mg of 2,6-pyridine dicarboxylic acid, 173 mg of N-HydroxySuccinimide (NHS), 287 mg of N-(3-dimethylaminopropyl)-N'-EthylCarboDiimide (EDC) hydrochloride are inserted in 5 ml of water whose pH is adjusted to be 8 (solution A). After 1 hour, 350 ml of APTES is added to the solution which is vigorously agitated for 90 minutes.

In a 100 ml Erlenmeyer flask, 2.27 ml of Triton X-100 (surfactant), 2.31 ml of n-hexanol (co-surfactant), 9.61 ml of cyclohexane, and 0.60 ml of the solution A are inserted and vigorously agitated. After 5 minutes, 0.060 ml of APTES and 0.200 ml of TEOS are added to the microemulsion.

The silica polymerization reaction is completed by the addition of 0.050 ml of $NH_4OH$ after 30 minutes. The microemulsion system is maintained during 24 hours under agitation at room temperature. After 24 hours, the particles formed are recovered by precipitation in centrifugation tubes by adding the same volume of ethanol for each wash. The washes are repeated 3 times with absolute ethanol. The obtained powder is finally dispersed in 20 ml of distilled water, then 360 mg of $TbCl_3$ is added.

PREPARATION 5. GRAFTING OF PHOSPHONATE FUNCTIONS ON PARTICLES OF SILICA (DIAMETER 64 NM) ENCAPSULATING FLUORESCEIN MOLECULES

In a 2.5 ml bottle, 20 mg of FITC and of APTES are inserted and vigorously agitated. After 30 minutes of homogenization at room temperature, the synthesis by microemulsion can begin.

In a 100 ml Erlenmeyer flask, 2.27 ml of Triton X-100 (surfactant), 2.31 ml of n-hexanol (co-surfactant), 9.61 ml of cyclohexane and 0.61 ml of water with a pH of 5.5 are inserted and vigorously agitated. After 5 minutes, 0.040 ml of solution containing the fluorescein is added to the microemulsion, then 0.020 ml of APTES and 0.289 ml of TEOS.

The silica polymerization reaction is completed by the addition of 0.173 ml of $NH_4OH$ after 30 minutes. The microemulsion system is maintained for 24 hours under agitation at room temperature. After 24 hours, 0.100 ml of TEOS and 0.050 ml of THPMP (3-TriHydroxysilylPropylMethylPhosphonate of sodium) are added to the microemulsion. After 24 hours under agitation, the particles formed are recovered by precipitation in centrifugation tubes by adding the same volume of ethanol for each wash. The washes are repeated three times with absolute ethanol. The obtained powder is finally dispersed in 20 ml of distilled water.

PREPARATION 6. GRAFTING OF UNCHARGED POLYETHYLENE-GLYCOL FUNCTIONS ON PARTICLES OF SILICA (DIAMETER 64 NM) ENCAPSULATING FLUORESCEIN MOLECULES

In a 2.5 ml bottle, 20 mg of FITC and of APTES are inserted and vigorously agitated. After 30 minutes of homogenization at room temperature, the synthesis by microemulsion can begin.

In a 100 ml Erlenmeyer flask, 2.27 ml of Triton X-100 (surfactant), 2.31 ml of n-hexanol (co-surfactant), 9.61 ml of cyclohexane (oil) and 0.61 ml of water with a pH of 5.5 are inserted and vigorously agitated. After 5 minutes, 0.040 ml of solution containing the fluorescein is added to the microemulsion, then 0.020 ml of APTES and 0.289 ml of TEOS (TetraEthOxyXilane).

The silica polymerization reaction is completed by the addition of 0.173 ml of a solution of $NH_4OH$ after 30 minutes. The microemulsion system is maintained for 24 hours under agitation at room temperature. After 24 hours, 0.100 ml of TEOS and 40 mg of mPEG-Si (methoxy-polyethylene-glycol-triethoxysilane) are added to the microemulsion. After 24 hours under agitation, the particles formed are recovered by precipitation in centrifugation tubes by adding the same volume of ethanol for each wash. The washes are repeated three times with absolute ethanol. The obtained powder is finally dispersed in 20 ml of distilled water.

PREPARATION 7. GRAFTING OF AMINE FUNCTIONS ON PARTICLES OF SILICA (DIAMETER 64 NM) ENCAPSULATING FLUORESCEIN MOLECULES

In a 2.5 ml bottle, 20 mg of FITC and of APTES are inserted and vigorously agitated. After 30 minutes of homogenization at room temperature, the synthesis by microemulsion can begin.

In a 100 ml Erlenmeyer flask, 2.27 ml of Triton X-100 (surfactant), 2.31 ml of n-hexanol (co-surfactant), 9.61 ml of cyclohexane and 0.61 ml of water with a pH of 5.5 are inserted and vigorously agitated. After 5 minutes, 0.040 ml of solution containing the fluorescein is added to the microemulsion, then 0.020 ml of APTES and 0.289 ml of TEOS.

The silica polymerization reaction is completed by the addition of 0.173 ml of a solution of $NH_4OH$ after 30 minutes. The microemulsion system is maintained for 24 hours under agitation at room temperature. After 24 hours, 0.100 ml of TEOS and 0.100 ml of TMPTA (N-TriMethoxysilylPropyl-N,N,N-TrimethylAmmonium chloride) are added to the microemulsion. After 24 hours under agitation, the particles formed are recovered by precipitation in centrifugation tubes by adding the same volume of ethanol for each wash. The washes are repeated three times with absolute ethanol. The obtained powder is finally dispersed in 20 ml of distilled water.

PREPARATION 8. PREPARATION OF A SOLID MEDIUM CONSTITUTED BY A CARTRIDGE OF POROUS CORE

The preparation 8 consists in fabricating a cartridge allowing for a fluid to diffuse through a cylindrical core of porous rock in the longitudinal direction, without fluid loss on the side of the latter. The equipment used is composed of the core, two plugs having the same diameter, machined specifically for threaded, of a tube made of transparent polyvinyl chloride (PVC), of a pattern made of PolyTetraFluoroEthylene (PTFE), of Araldite® glue, and of a tube of commercial silicon joint.

Push down one of the two plugs in the pattern, fix it with silicone, and then let dry for 30 minutes. Prepare the Araldite® glue in a small aluminum cup, then place the core on the plug and glue it, let dry for a few minutes. Do the same with the top plug. Cut the PVC tube to the corresponding length, put some silicone on the base of the tube, then turn it over on the pattern. Place everything in an incubator at 50° C. for ½ hour.

Determine the volume of epoxy resin taking into account the phenomenon of imbibition in the rock (volume equivalent to 0.4 cm of diameter of the column) The epoxy resin is composed at 70% of a resin base (Epon® 828—Miller-Stephenson Chemical Company, Inc) and at 30% of a hardener (Versamid® 125—Miller-Stephenson Chemical Company, Inc). In a tumbler, mix the resin with the hardener for 10 minutes, then place the mixture at 50° C. for 40 to 50 minutes until a transparent and fluid mixture has been obtained. Slowly poor the mixture along the PVC tube, then leave at room temperature for two hours. Then, place the assembly at 70° C. for two hours.

PREPARATION 9. PREPARATION OF A SUSPENSION OF NANOPARTICLES

The preparation 9 is a diluted suspension of nanoparticles in sea water, which is the fluid used for the tests of diffusion through a porous core.

A synthetic sea water solution is composed of demineralized water in which the following salts have been dissolved:

| Salt | Concentration (g/L) |
| --- | --- |
| NaCl | 24.80 |
| KCl | 0.79 |
| $MgCl_2$ | 5.25 |
| $CaCl_2$ | 1.19 |
| $NaHCO_3$ | 0.20 |
| $Na_2SO_4$ | 4.16 |

Concentrated suspensions of nanoparticles according to the examples of preparation 1 to 7, are implemented. A certain quantity of these suspensions is diluted in a volume of sea water of 500 mL so as to end up with a final concentration in particles comprised between 5 and 20 mg/L. To this suspension, 0.5 g of potassium iodide is added, the potassium iodide having a 1 tracer behavior that is idea for the diffusion tests. The final suspension is then vacuum-degassed for 5 to 10 minutes.

PREPARATION 10. ASSEMBLY FOR THE DIFFUSION OF A SUSPENSION OF NANOPARTICLES THROUGH A SOLID MEDIUM FORMED BY A CORE ACCORDING TO PREPARATION 8—OPERATION OF THIS ASSEMBLY

The assembly allowing for testing the diffusion of nanoparticles through a porous rock core and the functioning of this assembly are described here. A diluted suspension of particles according to preparation 1. A cartridge containing the porous rock is prepared according to preparation 8.

The assembly is composed of a dual syringe pump allowing for fixing a flow rate comprised between 1 and 1000 mL per hour. The latter pumps the suspension of particles and directs it toward the cartridge containing the porous rock. The fluid diffuses through the latter, the differential pressure on both sides of the rock is monitored by a sensor. The fluid is finally directed toward a fraction collector.

What is measured with these fractions is, on the one hand, the UV absorption at $\lambda=254$ nm of the fluid. The latter is very low when the fluid contains no iodide and becomes more important when the latter is present. The UV absorption at: $=254$ nm thus makes it possible to follow the diffusion of the ideal tracer. On the other hand, in the case of nanoparticles prepared according to the examples of preparation 1 or 2 or 5 or 6 or 7, the fluorescence is measured at $\lambda=515$ nm (excitation at 475 nm). The latter thus makes it possible to follow the diffusion of the particles.

If several experiments are carried out on the same core, a step of counter-current washing by passage of a quantity greater than 500 mL of sea water obtained according to preparation 2 and without tracer, is provided.

Example 1

Particles Prepared According to the Example of Preparation 1; Naked $SiO_2$ Surface This example is a test of diffusion through a porous core cartridge according to preparation 8. The porous core is of the DU30804 type and has the following characteristics:

Nature of the material: sandstone
Dimensions: 4 to 5 cm in diameter; 10 to 13 cm in length
Permeability: 250 to 500 mDa
Porosity: 20%

The suspension of nanoparticles has been obtained according to preparation 9. The flow rate imposed by the pump is 20 mL/hour. The fractions recovered at the exit of the rock have a volume of 5 mL.

Figure 3:
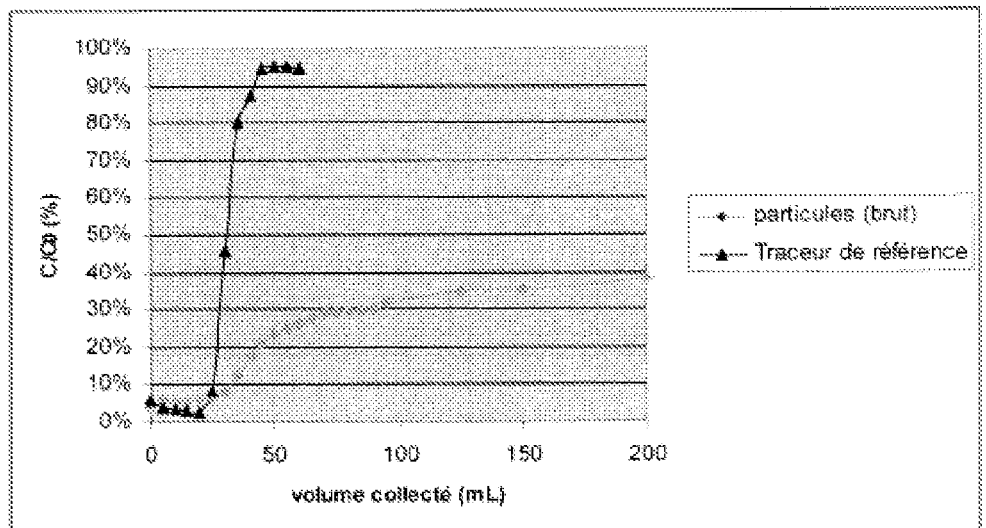
FIG. 3 shows the comparative curves of diffusion between the reference tracer (yellow) and the nanoparticles prepared according to example 1. On the ordinate, the absorption at 254 nm or the fluorescence at 515 nm, standardized to initial values. (% H represents the percentage of the height of the emission peak).

FIG. 3 shows the comparative curves of diffusion between the reference tracer (yellow) and the nanoparticles prepared according to the example of preparation 1.

Example 2

Particles Prepared According to the Example of Preparation 5; $SiO_2$ Surface Grafted with Propyl-Methylphosphonates Groups This example is a test of diffusion through a porous core cartridge according to preparation 8. The porous core is of the DU30804 type and has the following characteristics:

Nature of the material: sandstone
Dimensions: 4 to 5 cm in diameter; 10 to 13 cm in length
Permeability: 250 to 500 mDa
Porosity: 20%

The suspension of nanoparticles has been obtained according to preparation 9. The flow rate imposed by the pump is 20 mL/hour. The fractions recovered at the exit of the rock have a volume of 5 mL.

Figure 4:
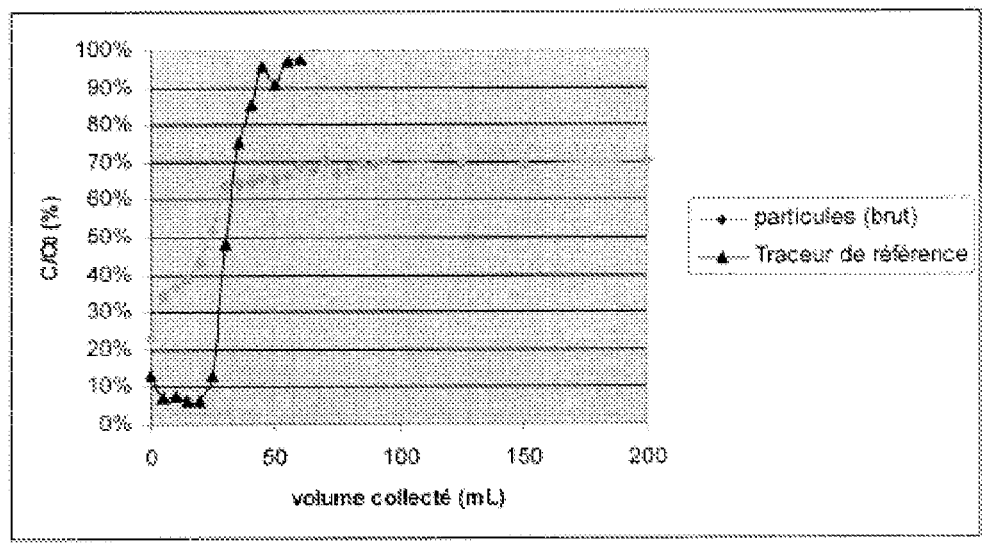
FIG. 4 shows the comparative curves of diffusion between the reference tracer (yellow) and the nanoparticles prepared according to example 2. On the ordinate, the absorption at 254 nm or the fluorescence at 515 nm, standardized to initial values.

FIG. 4 shows the comparative curves of diffusion between the reference tracer (yellow) and the nanoparticles prepared according to the example of preparation 5.

Example 3

Particles Prepared According to the Example of Preparation 6; SiO$_2$ Surface Grafted with Polyethylene-Glycol, O-Methyl Groups This example is a test of diffusion through a porous core cartridge according to preparation 8. The porous core is of the DU30804 type and has the following characteristics:
Nature of the material: sandstone
Dimensions: 4 to 5 cm in diameter; 10 to 13 cm in length
Permeability: 250 to 500 mDa
Porosity: 20%
The suspension of nanoparticles has been obtained according to preparation 9. The flow rate imposed by the pump is 20 mL/hour. The fractions recovered at the exit of the rock have a volume of 5 mL.

Figure 5:
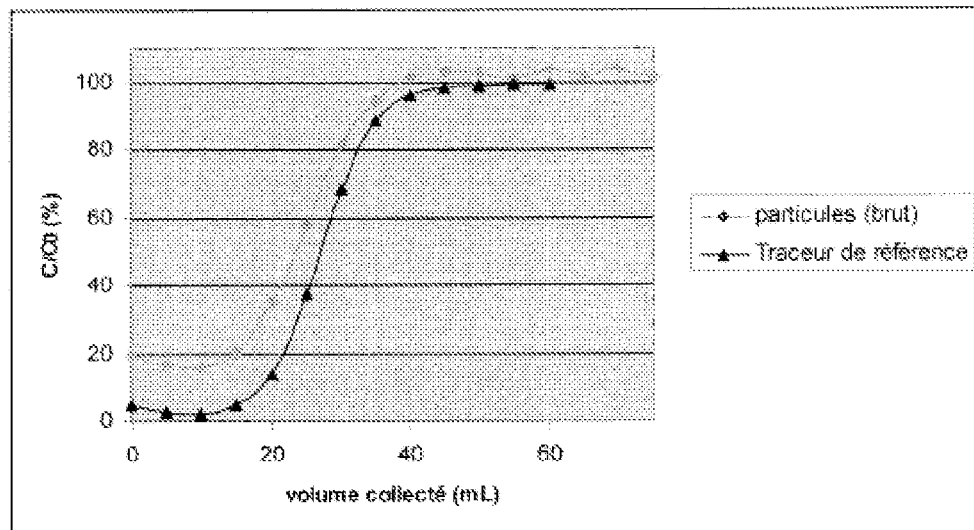
FIG. 5 shows the comparative curves of diffusion between the reference tracer (yellow) and the nanoparticles prepared according to example 3. On the ordinate, the absorption at 254 nm or the fluorescence at 515 nm, standardized to initial values.

FIG. 5 shows the comparative curves of diffusion between the reference tracer (yellow) and the nanoparticles prepared according to the example of preparation 6.

Example 4

Particles Prepared According to the Example of Preparation 7; SiO2 Surface Grafted with Propylamine Groups This example is a test of diffusion through a porous core cartridge according to preparation 8. The porous core is of the DU30804 type and has the following characteristics:
Nature of the material: sandstone
Dimensions: 4 to 5 cm in diameter; 10 to 13 cm in length
Permeability: 250 to 500 mDa
Porosity: 20%
The suspension of nanoparticles has been obtained according to preparation 9. The flow rate imposed by the pump is 20 mL/hour. The fractions recovered at the exit of the rock have a volume of 5 mL.

Figure 6:
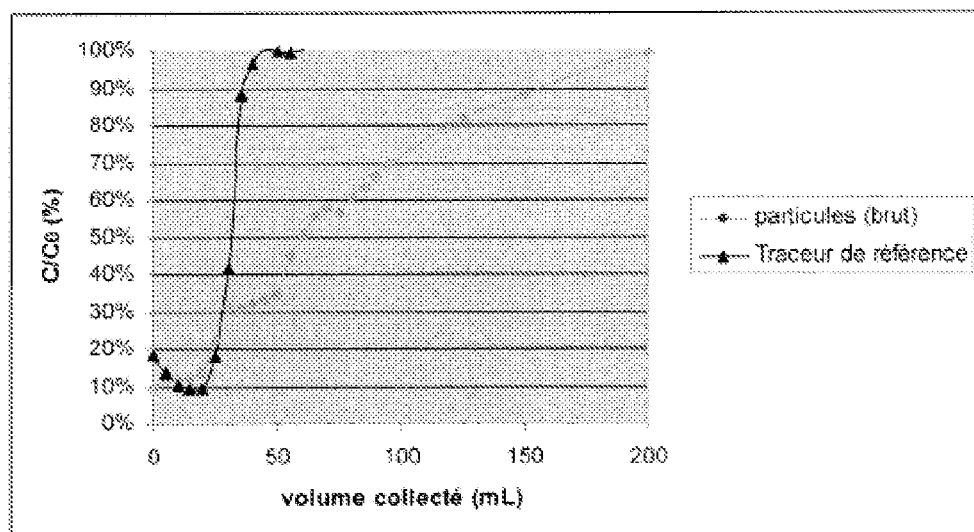
FIG. 6 shows the comparative curves of diffusion between the reference tracer (yellow) and the nanoparticles prepared according to example 4. On the ordinate, the absorption at 254 nm or the fluorescence at 515 nm, standardized to initial values.

FIG. 6 shows the comparative curves of diffusion between the reference tracer (yellow) and the nanoparticles prepared according to the example of preparation 7.

Comments: the curves 3 to 6 show the comparative curves of diffusion between the reference tracer (yellow) and the nanoparticles obtained according to the preparations 1, 5, 6, and 7, respectively. It is clearly shown that the particles corresponding to FIG. 5, that is, the particles according to preparation 6, behave like an ideal tracer under these conditions. A portion of the particles corresponding to FIG. 4, that is, corresponding to preparation 5, also behave like an ideal tracer.

The invention claimed is:

1. A method of studying an oil reservoir by diffusion of a fluid through said solid medium, comprising:
    injecting, in-the oil reservoir, an injection liquid comprising a nanoparticle-based tracer; each nanoparticle
    having average dimensions comprised, between 20 and 200 nm;
    emitting one or several signals S detectable at dilutions of less than or equal to $10^{-7}$, said signals S being emitted by fluorescent compounds, chemiluminescent compounds, or noble metals, and measured by chemical analysis, ICP, magnetic analysis, susceptibility measurement, measures of transition temperatures, or analysis of FC/ZFC curves;
    being adapted to form a stable colloidal suspension in a saline medium;
    wherein said nanoparticles is constituted of a core and a coating, said coating comprising at least one organic or organosilicon component and wherein the hydrophilic-lipophilic balance or the Zeta potential of said creates a repulsion and limits interactions with the solid medium;
    recovering the liquid having diffused;
    analyzing this liquid having diffused to measure the quantity of tracer by detection of the signal or signals S,
    wherein the core of the nanoparticles contains:
        at least one material selected from the group consisting of: the semiconductors, noble metals, fluorides, vanadates or rare earth oxides, and their mixtures;
        at least a matrix, selected from the group of materials consisting of: silicas, polysiloxanes, aluminas, zirconias, aluminates, aluminophosphates, metal oxides and their mixtures, this matrix including, inside or at its surface:
            i. luminescent entities selected from the group consisting of: the semiconductors, oxides, rare earth fluorides or vanadates, organic fluorescent molecules, transition metal ions, rare earth ions, and their mixtures optionally associated to complexing molecules or to molecules allowing for enhancing their absorption and their mixtures;
            ii. optionally, other entities allowing for modifying the luminescence properties and selected from the group consisting of: noble metal particles, their mixtures and their alloys.

2. A method according to claim 1, wherein the coating of the nanoparticles comprises R-radicals grafted by covalence, based on surface silanes Si—R connections originating from:
    v. charged hydrophilic compounds;
    vi. neutral hydrophilic compounds;
    vii. a hydrophobic polymer; or,
    viii. of mixtures thereof.

3. A method according to claim 2, wherein the nanoparticle coating comprises grafted R-radicals at the rate of at least one R-radical for 10 nm$^2$ of surface.

4. The method of claim 2, wherein said charged hydrophilic compounds have a molecular mass of less than 5,000 g/mol and selected from the organic compounds consisting of at least one of the following functions: alcohol, carboxylic acid, amine, amide, ester, ether oxide, sulfonate, phosphonate and phosphinate, and mixtures thereof.

5. The method of claim 2, wherein said charged hydrophilic compounds have a molecular mass of less than 450 g/mol.

6. The method of claim 2, wherein said neutral hydrophilic compounds are selected from the group consisting of a polyalkylene glycol, Diethylene-TriaminePentaAcetic acid (DTPA), dithiolate DTPA (DTDTPA) or succinic acid, and the mixtures of these neutral hydrophilic compounds.

7. A method according to claim 1, wherein prior to the analysis of the liquid having diffused, the latter is concentrated.

8. A method according to claim 1 wherein, to measure the quantity of tracer in the liquid having diffused, a detection by an analytical method selected from fluorescence, chemical analysis, ICP, magnetic analysis is carried out.

9. A method according to claim 1, wherein, to measure the quantity of tracer in the liquid having diffused, one proceeds at least with one detection by time-resolved fluorescence, that is, triggered with delay after excitation (i.e. a few microseconds), which eliminates a large portion of the luminescence, intrinsic to the studied solid medium and measures only that relative to the tracing nanoparticle.-

10. A method according to claim 1 wherein each nanoparticles emits at least two signals to be detected:
   a signal S1 that is emitted by fluorescent compounds or by chemiluminescent compounds and measured by fluorescence or by chemilumiescence;
   a signal S2 that is emitted by a noble metal, such as gold, silver, platinum, and their mixtures and/or alloys, and measured by chemical analysis, ICP, magnetic analysis, susceptibility measurement, measures of transition temperatures, or by analysis of FC/ZFC curves;
   said noble metal constituting the core of the nanoparticle.

11. The method of claim 1, wherein the core of the nanoparticles contains at least one material selected from the group consisting of the lanthanides, their alloys and their mixtures.

12. The method of claim 11, wherein said lanthanides are selected from the sub-group consisting of: Pr, Nd, Sm, Eu, Tb, Dy, Ho, Er, Tm, and Yb, their alloys and their mixtures.

13. A method of evaluating the volume of oil in reserve in the oil reservoir comprising:
   (i) injecting into an oil reservoir, a nanoparticle-based tracer; each nanoparticule having average dimensions comprised, between 20 and 200 nm;
      emitting one or several signals S detectable at dilutions of less than or equal to $10^{-7}$ said signals S being emitted by fluorescent compounds, chemiluminescent compounds, or noble metals and detectable by chemical analysis, ICP, magnetic analysis, susceptibility measurement, measures of transition temperatures, or analysis of FC/ZFC curves;
      forming a stable colloidal suspension in a saline medium;
   wherein said nanoparticle is constituted of a core and a coating, said coating comprising at least one organic or organosilicon component, and wherein the hydrophilic-lipophilic balance or the Zeta potential of said coating creates a repulsion and limits interactions with the solid medium, and,
   (ii) monitoring flow between the injection well and the production well,
   (iii) evaluating the volume of oil in reserve in the oil reservoir, wherein the core of the nanoparticles contains:
      at least one material selected from the group consisting of: the semiconductors, noble metals, fluorides, vanadates or rare earth oxides, and their mixtures;
      at least a matrix, selected from the group of materials consisting of: silicas, polysiloxanes aluminas, zirconias, aluminates, aluminophosphates, metal oxides and their mixtures, this matrix including, inside or at its surface:
         i. luminescent entities selected from the group consisting of: the semiconductors, oxides, rare earth fluorides or vanadates, organic fluorescent molecules, transition metal ions, rare earth ions, and their mixtures optionally associated to complexing molecules or to molecules allowing for enhancing their absorption and their mixtures;
         ii. optionally, other entities allowing for modifying the luminescence properties and selected from the group consisting of noble metal particles, and their mixtures.

14. An injection liquid for use in an oil reservoir, said injection liquid, comprising water and nanoparticles, each nanoparticle:
   having dimensions comprised between 20 and 200 nm;
   being capable of emitting one or several signals S detectable at dilutions of less than or equal to $10^{-7}$, said signals S being emitted by fluorescent compounds, chemiluminescent compounds, or noble metals, and measured by chemical analysis, ICP, magnetic analysis, susceptibility measurement, measures of transition temperatures, or analysis of FC/ZFC curves;
   forming a stable colloidal suspension in a saline medium;
   wherein said nanoparticles is constituted of a core and a coating, said coating comprising:
   at least one organic or organosilicon component, and
   R-radicals grafted, by covalence, based on surface silanes Si—R connections originating from neutral hydrophilic compounds;
   said core containing at least a matrix consisting of silicas, and wherein the hydrophilic-lipophilic balance or the Zeta potential of said coating creates a repulsion and limits interactions with the solid medium,
   wherein the core of the nanoparticles contains at least one material selected from the group consisting of: the semiconductors, noble metals, fluorides, vanadates or rare earth oxides, and their mixtures; and the matrix includes inside or at its surface:
      i. luminescent entities selected from the group consisting of: the semiconductors, oxides, rare earth fluorides or vanadates, organic fluorescent molecules, transition metal ions, rare earth ions, and their mixtures optionally associated to complexing molecules or to molecules allowing for enhancing their absorption and their mixtures;
      ii. optionally, other entities allowing for modifying the luminescence properties and selected from the group consisting of: noble metal particles, their mixtures and their alloys.

15. The injection liquid of claim 14, wherein the core of the nanoparticles contains at least one material selected from the group consisting of the lanthanides, their alloys and their mixtures.

16. The injection liquid of claim 15, wherein said lanthanides are selected from the sub-group consisting of: Pr, Nd, Sm, Eu, Tb, Dy, Ho, Er, Tm, and Yb, their alloys and their mixtures.

17. The injection liquid of claim 14, wherein said neutral hydrophilic compounds are selected from the group consisting of a polyalkylene glycol, Diethylene-TriaminePentaAcetic acid (DTPA), dithiolate DTPA (DTDTPA) or succinic acid, and the mixtures of these neutral hydrophilic compounds.

* * * * *